United States Patent [19]

Ogan et al.

[11] Patent Number: 4,816,123
[45] Date of Patent: Mar. 28, 1989

[54] METHOD OF FABRICATING CAPILLARY ELECTROPHORESIS SEPARATION CHANNELS

[75] Inventors: Kenneth Ogan, Newtown, Conn.; Frans M. Everaerts; Theo P. E. M. Verheggen, both of Weert, Netherlands

[73] Assignee: The Perkin-Elmer Corporation, Norwalk, Conn.

[21] Appl. No.: 51,808

[22] Filed: Jul. 6, 1987

Related U.S. Application Data

[62] Division of Ser. No. 852,488, Apr. 16, 1986, abandoned.

[51] Int. Cl.[4] .................. G01N 27/28; B29C 39/02
[52] U.S. Cl. .................. 204/183.3; 204/299 R; 264/313; 264/317
[58] Field of Search .................. 204/183.3, 299 R; 264/317, 313, 272.11, 272.14; 210/198.3, 198.2

[56] References Cited

U.S. PATENT DOCUMENTS

| 240,459 | 4/1981 | Quinby | 264/313 X |
| 805,260 | 11/1905 | Callan | 264/313 X |

FOREIGN PATENT DOCUMENTS

| 56-164827 | 12/1981 | Japan | 264/317 |
| 61-002541 | 1/1986 | Japan | 264/317 |
| 563192 | 8/1944 | United Kingdom | 264/317 |
| 710453 | 6/1954 | United Kingdom | 264/313 |
| 760596 | 11/1956 | United Kingdom | 264/313 |
| 2084070 | 4/1982 | United Kingdom | 264/313 |

OTHER PUBLICATIONS

F. Foret et al., "On-line fiber optic UV detection cell and conductivity cell for capillary zone electrophoresis", Electrophoresis 1986, 7, pp. 430–432.

*Primary Examiner*—John F. Niebling
*Assistant Examiner*—John S. Starsiak, Jr.
*Attorney, Agent, or Firm*—Francis L. Masselle; Ronald G. Cummings; Edwin T. Grimes

[57] ABSTRACT

The basic concept of this invention involves the use of a wire or capillary tube as a template strand. The outside diameter and shape of the template strand correspond to the inside diameter and shape of a desired separation capillary. A detector may be incorporated by providing a pair of electrode wires, or the ends of a pair of optical fibers, and pressing them against opposite sides of the template. As plastic is then polymerized around this asssembly by casting or molding. The template is then removed, leaving a capillary channel with a sidewall incorporating the wire electrodes and optical fibers. Using this method, it is possible to form a single unit including a separation capillary, conductivity detector, and spectroscopy detector.

12 Claims, 4 Drawing Sheets

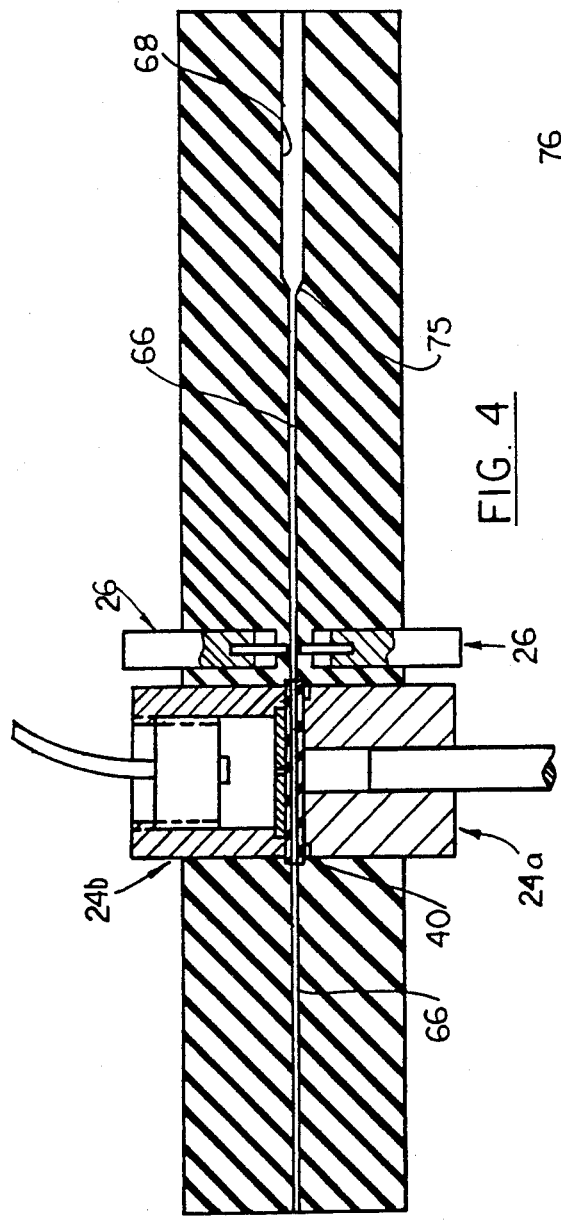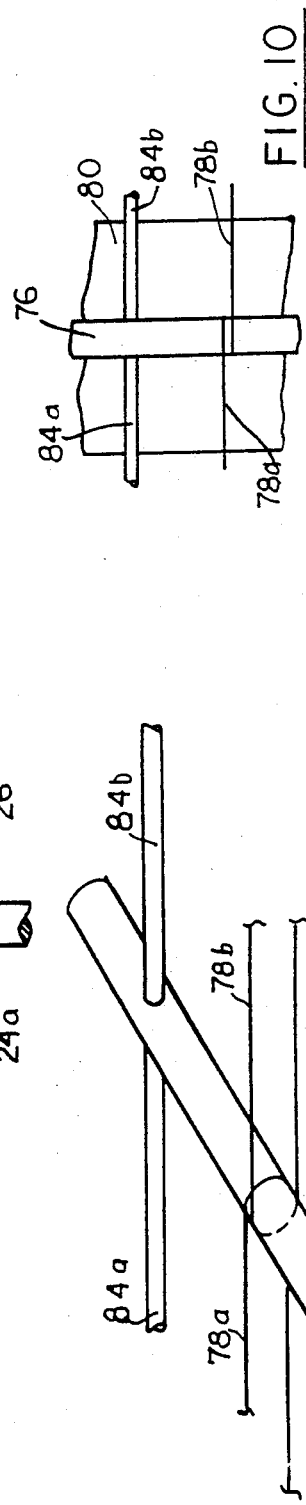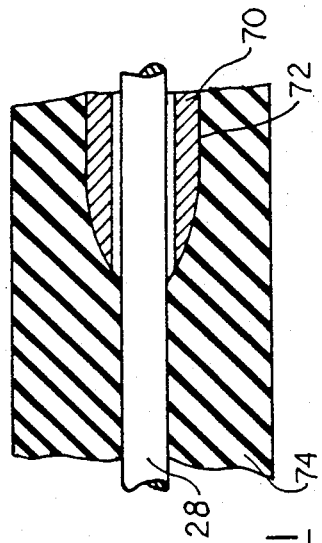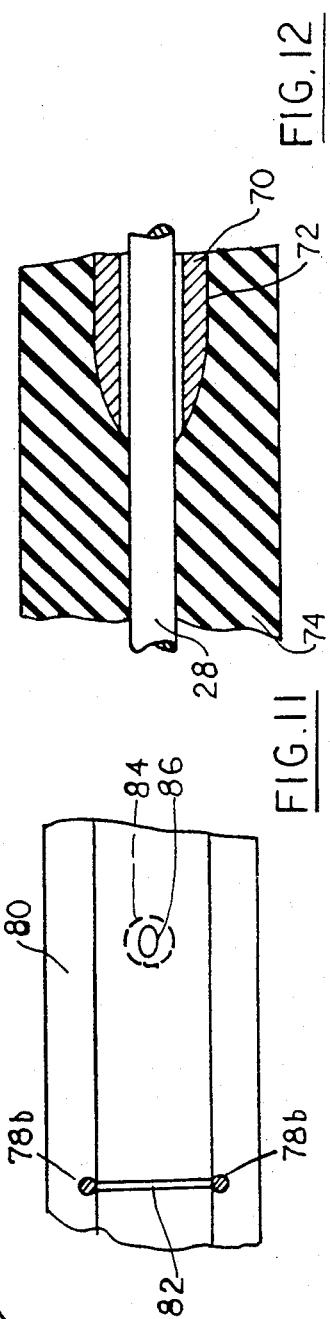

METHOD OF FABRICATING CAPILLARY ELECTROPHORESIS SEPARATION CHANNELS

This application is a division of Ser. No. 852,488 filed Apr. 16, 1986 and now abandoned.

TECHNICAL FIELD

This invention relates to the design and construction of separation channels and detectors for use in electrophoresis, as exemplified by zone electrophoresis and isotachophoresis (ITP).

BACKGROUND ART

Resolution in isotachophoresis or capillary zone electrophoresis is controlled by the diameter of the separation channel. Resolution changes with the square of the ratio of an initial diameter a second (i.e., changed) to diameter of the separation channel. Therefore, as small an operating diameter as possible is sought. The design and construction of the detectors for such systems provide the practical limit for reduction of the diameter of the separation channel. Commercially available capillary electrophoretic instruments use 0.3 mm to 0.5 mm diameter capillaries, but Everaerts, Beckers and Verheggen (Isotachophoresis, Elsevier Scientific Publ. Co., Amsterdam, 1976, p. 395) describe the construction of an instrument embodying a 0.2 mm diameter separation channel (i.e., a 2.25 to 6-fold improvement in resolution). These authors also describe the construction of the detectors for such a system, detectors which require difficult and mechanically challenging construction techniques.

The detectors of choice for modern capillary electrophoretic analysis separations are the conductivity detector and the UV absorbance detector. These detectors should be mounted directly in the separation channel in order to retain the high resolution obtained by use of very small separation channels (0.2 mm in diameter or smaller). This places stringent demands on the introduction of light transverse to the separation channel for the UV absorbance detector. The large voltage gradient utilized for isotachophoresis or capillary zone electrophoresis also places severe restrictions on the width of the electrodes in contact with the separation channel in the conductivity detector. Thus, for a 15000 V gradient applied across a 20 cm long separation channel of 0.2 mm ID, the electrodes must be less than 10 $\mu$m thick; otherwise electrolysis occurs at the extreme edges of each electrode. For the same reason electrodes must also be precisely perpendicular to the axis of the separation channel.

It is a primary object of the present invention to provide an improved means of constructing the conductivity and optical detectors for use in small bore isotachophoresis or capillary electrophoresis. One prior art technique for making a simple conductivity detector employs hot platinum wires melted through the wall of the polytetrafluoroethylene (PTFE) capillary used for the isotachophoretic separation channel. This is described by Kaniansky, et al. 267 *Journal of Chromatography* 67 (1983).

It is total *volume* of the separation channel which is important in an isotachophoretic separation rather than the *length* of the channel. Accordingly, volume coupling may be employed as disclosed by Verheggen and Everaerts, 249 *Journal of Chromatography* 221 (1982). The construction of a volume coupling system as described by Verheggen and Everaerts requires several interconnections between capillaries of different size, with the attendant problems of alignment and sealing.

Another object of the present invention is to provide a method for easily producing volume coupling in combination with the detectors and separation channel described. Other objects, features, and advantages will be apparent from the following description and appended claims.

BRIEF DESCRIPTION OF DRAWINGS

FIG. 4 is a cross-section taken substantially along the line 4—4 of FIG. 3 during a further stage of construction;

FIG. 9 is an isometric view of an alternative method of forming electrodes and optical detectors in accordance with the present invention;

FIG. 10 is a top view of the apparatus of FIG. 9;

FIG. 11 is an enlarged longitudinal cross-section taken through the detector produced by the apparatus of FIGS. 9 and 10; and FIG. 12 is an enlarged cross-section illustrating the formation of a volume coupling portion of the device of FIG. 4.

BEST MODE FOR CARRYING OUT THE INVENTION

The basic concept of this invention involves the use of a strand of wire or capillary tube as a template for the separation channel. The outside diameter and shape of the template correspond to the inside diameter and shape of a desired separation capillary. A pair of component-detecting fibers such as electrode wires or optical elements are pressed against the template in diametric opposition. A plastic material is then polymerized around this assembly by casting or molding. The template is then removed, leaving a capillary channel having a wall surface which includes the wire electrodes and/or optical elements. Thus, the separation capillary, conductivity detector, and spectroscopy detectors are all assembled as a single unit, eliminating the problems associated with capillary connections to the detectors and to the rest of the system.

Figure 1:
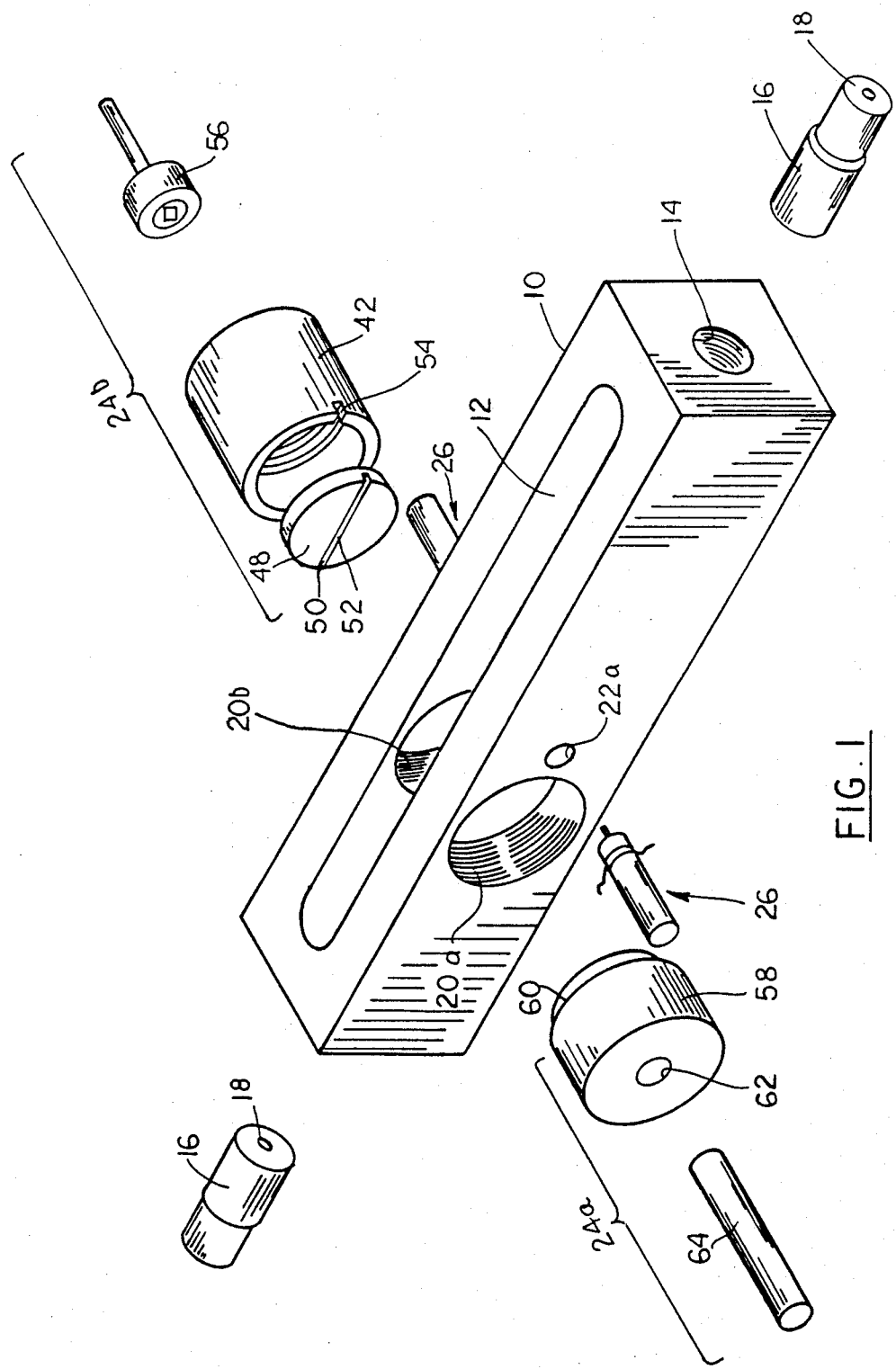
FIG. 1 is an exploded isometric view of one apparatus suitable for practicing the invention.

Referring now to FIG. 1, there is illustrated a plastic mold form 10 which may be of any desired shape but is shown here as a right rectangular parallelepiped. It defines a central cavity 12 and a pair of aligned openings 14 (one only appearing in FIG. 1) extend through its end walls. A pair of plastic plugs 16 are insertable into the openings 14 and each includes a small diameter hole 18 to frictionally engage a template, as will be explained presently. The sidewalls of mold form 10 define a pair of coaxially aligned, relatively large holes 20a, 20b and a pair of similarly aligned but relatively smaller holes 22a, 22b.

An optical assembly is formed from a male 24a and a female 24b sub-assembly which are insertable through the holes 20a, 20b. These assemblies will be described later in more detail. A pair of similar electrode assemblies 26 are insertable through the holes 22a, 22b.

Figure 2:
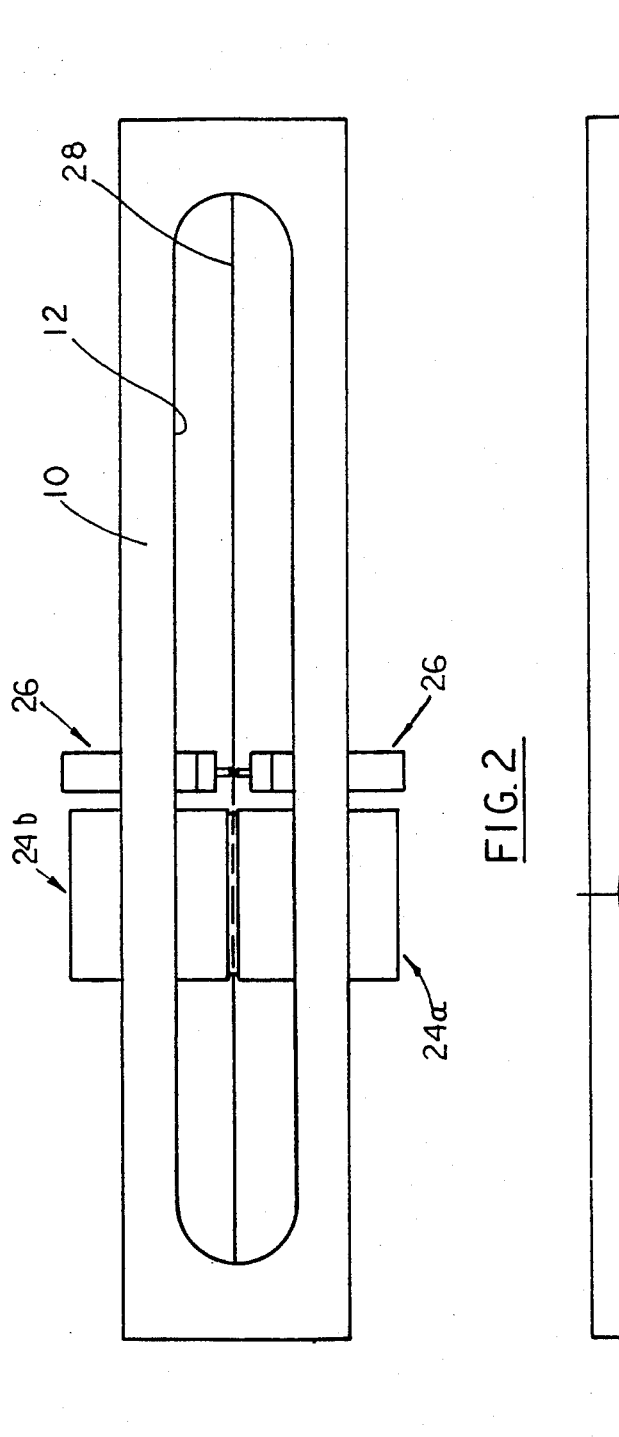
FIG. 2 is a top view of the apparatus of FIG. 1, assembled with a template wire in place.
Figure 3:
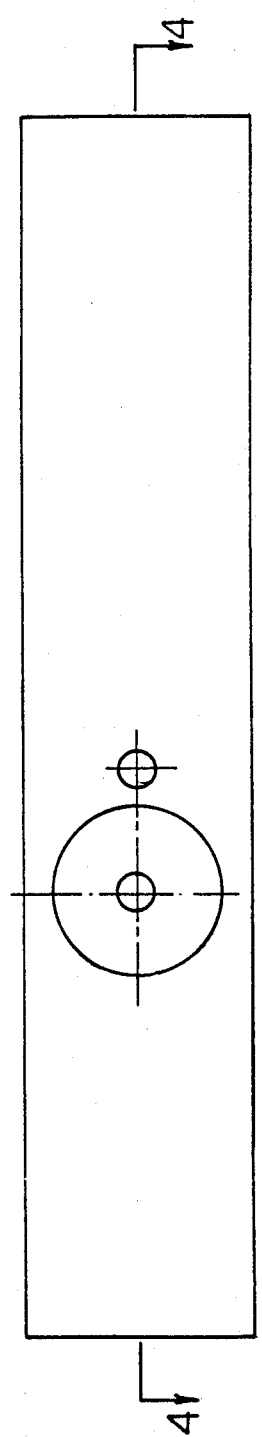
FIG. 3 is a side view of the apparatus of FIG. 2.

In practicing this invention, a template wire 28 (FIG. 2) is threaded through the holes 18 in plugs 16. The plugs are inserted into the openings 14 in the ends of mold cavity 12, thereby supporting the template in the cavity as shown in FIG. 2. The template wire may be of any desired material such as, for example, steel to which a release agent has been applied or a material such as polytetrafluroethylene (PTFE) which would require no release agent. A typical diameter for the template wire 28 might be 0.2 mm.

Figure 5:
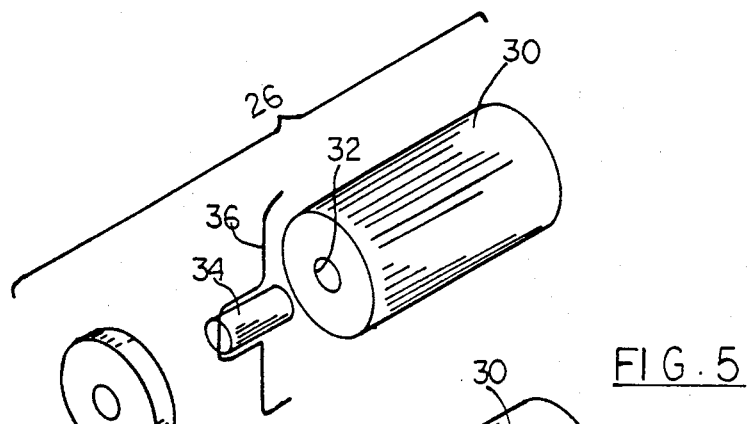
FIG. 5 is an exploded isometric view of an electrode assembly in accordance with the invention.
Figure 6:
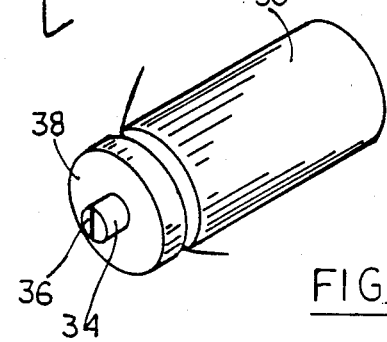
FIG. 6 is a view similar to FIG. 5 with the parts assembled.
Figure 7:
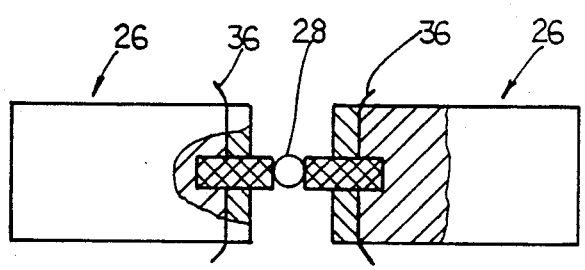
FIG. 7 is a view illustrating the function of the electrode assemblies.

Turning now to FIGS. 5 and 6, the construction of the electrode assemblies 26 will be described. Each comprises a cylindrical brass body 30 having a coaxial blind bore 32 at one end. A plastic pin 34 is inserted into bore 32 and a small diameter platinum wire 36 is positioned over the end of pin 34 in the manner illustrated. A brass washer 38 is then positioned over the pin 34 to form the completed assembly of FIG. 6. Electrode assemblies 26 are inserted into the holes 22a, 22b so that the platinum wires 36 contact the template wire 28 on each side as illustrated in FIG. 7. Because wires 36 make essentially point contact with the template wire 28 on diametrically opposite sides, precise vertical alignment of wires 36 is not required.

To provide an optical detector, a transparent, tubular plastic sleeve 40 (FIG. 8) is positioned over the template wire 28 in a medial segment thereof, VIZ.) the region between the large holes 20a, 20b in the sides of mold form 10. Optical sub-assembly 24b comprises a cylindrical brass body 42 having a female flange 44 around one end and an internal shoulder 46. Against the shoulder 46 is positioned an optically opaque member in the form of a thin disc 48. The disc 48 defines a (FIG.1) diametric slot 50 dimensioned so as to just receive the tubular sleeve 40 on the template wire 28. A small central hole 52 defines an optical aperture in disc 48 permits the passage of light into cylindrical hollow body 42. The flange 44 on body 42 includes a pair of slots 54 to accept the sleeve 40. Mounted within the hollow body 42 is a light detector 56.

Figure 8:
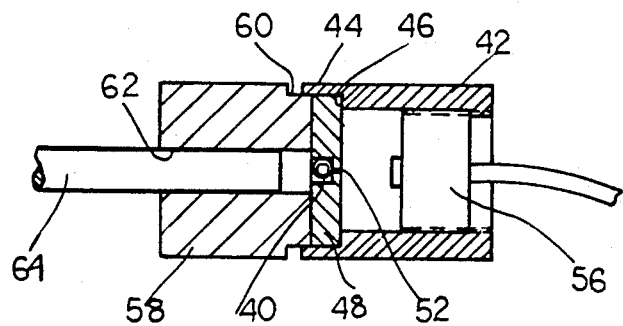
FIG. 8 is a cross-section of the ultraviolet detector portion of the invention.

Extending through the hole 20a on the opposite side of mold 10 is sub-assembly 24a comprising a cylindrical brass body 58 having a reduced diameter end or post 60. Post 60 projects into the flange 44 so that the sub-assemblies 24a, 24b engage opposite sides of the tubular sleeve 40 as shown in FIG. 8. A coaxial bore 62 in body 58 houses a light-transmitting member such as the end of an illuminated light pipe in the form of a quartz rod 64.

After the various elements are assembled, cavity 12 of the mold form 10 is filled with a suitable polymerizable plastic material in fluid or pliable state. After the plastic has hardened, the template wire 28 is removed by pulling it out of the polymerized plastic, thus leaving a capillary channel 66 which includes the electrode wires 36 actually forming a portion of the channel sidewall. What were formerly individual plastic elements, such as mold body 10, plugs 16 and sleeve 40 are now a single body as the cross-hatching in FIG. 4 indicates. In view of the fact that the fluid plastic flows in and around the electrode wires, only a very small portion of each wire's surface is actually exposed to the contents of the capillary channel.

Longitudinally displaced along the channel 66 from the electrode assemblies 26 are the optical sub-assemblies 24a, 24b. It will be apparent that an optical path is provided from the light source 64 through the sleeve 40 and the opening 52 to permit light to pass to the detector 56. In the embodiment having dimensions previously referred to, the actual diameter of the hole 52 was 0.24 mm, the slot 50 having a width of 0.35 mm.

A significant advantage of the method of this invention is that the volume coupling configuration can easily be incorporated. Volume coupling refers to the use of a two-stage or multiple stage capillary system in which the pre-separation occurs in a wider bore region 68, as shown in FIG. 4, and then a transition is made to a narrower bore capillary 66 which enhances resolution at the detector. As illustrated in FIG. 12, this may be accomplished by passing a length of steel capillary 70 over template wire 28. The end 72 of capillary 70 is bevelled as shown. The assembly is then cast in epoxy or other plastic 74 as previously described. After the epoxy sets, the steel capillary 70 is removed, along with the template wire 28, leaving a volume coupled region 75 as shown in FIG. 4. As a result of the tapered end 72, the two channel diameters are connected by a smooth transition zone.

Alternatively, the capillary and template may be interconnected by a conical coupling or a one-piece, plural diameter template may be employed.

In FIGS. 9-11, there are illustrated various modifications of the basic method described above. In place of a solid wire template, there is provided a capillary template 76. One advantage of employing a capillary as a template is that it may be removed by methods other than pulling, such as dissolution or melting, or by electrolytic or electrochemical means. (All such methods are included in the term "dissolution" as used in the claims.) This makes it possible to generate shapes and dimensions that are not feasible by conventional machining or molding techniques. For example, a long length of capillary could be contained in the same external length by coiling the template in a helical shape. As another example, the cross-section of the template could differ from a simple circular shape, possibly only in the detection region. An oval shape might be used to increase the optical path length for an optical absorbance detector.

FIGS. 9-11 also show an alternative technique for installing platinum wire electrodes 78a, b. Each electrode wire is passed around the template 76 and pulled in opposite directions, as illustrated, prior to potting in a resin 80. Upon removal of the template, there remains only a thin, semicircular electrode region 82, as shown in FIG. 11, on each side of the channel. The thinness of each region is again-due to the screening action of the polymer material. The degree of the screening will depend on the physical characteristics of the polymeric material, but permits use of slightly larger electrode wires since only a fraction of the full diameter is exposed to the electrical field gradient along the capillary zone. The fact that the two electrodes are slightly offset axially results in a potential gradient detector.

FIGS. 9 and 10 also illustrate a pair of optical fibers 84a, b. The optical quality ends of the fibers contact the template 76 diametrically opposite each other for the purpose of ultraviolet absorbance detection. Additional fibers may be added for fluorescence or multiple wavelength detection. After potting and removal of the template 76, there remains a direct window 86 into the capillary. This enables light to be introduced and monitored with very little loss as opposed to the conventional technique of shining light through the walls of PTFE capillaries. Furthermore, the window 86 is in the form of a natural optical slit, since the polymer flows around the template capillary except where the optical fiber makes tangential contact.

As used in the following claims, the term "electrophoresis" includes isotachophoresis, zone electrophoresis, moving boundary electrophoresis, and combinations of these.

This invention is also applicable to the detection of radioactive compounds by making at least one optical fiber of scintillation glass or of a material whose transmission characteristics are affected by nuclear radiation. It will be apparent to those skilled in the art that a number of other variations and modifications may be made in this invention without departing from its spirit and scope. Accordingly, the foregoing description is to be construed as illustrative only, rather than limiting. This invention is limited only by the scope of the following claims.

We claim:

1. The method of forming a capillary component for use in an electrophoresis instrument which comprises:
   providing a template strand having external profile dimensions and shape corresponding to the internal profile dimensions and shape of a desired capillary component;
   contacting a first point on the surface of said template strand with a first fiber capable of conducting a component-detecting medium;
   contacting a second point on the surface of said template strand substantially opposite said first point, with a second fiber capable of conducting said component-detecting medium;
   encasing said template strand within a body of hardenable material;
   hardening said hardenable material; and
   removing said template strand.

2. The method of claim 1 wherein said first and second fibers are wires and said component-detecting medium is electricity.

3. The method of claim 2 wherein each of said contacting steps comprises:
   wrapping said wire over the end of an applicator member; and
   pressing said applicator member and wire against the template strand.

4. The method of claim 2 wherein each of said contacting steps comprises:
   looping said wire over said template strand and exerting a pulling force on said wire to make intimate contact between said wire and strand over substantially one half the circumference of said strand.

5. The method of claim 1 wherein said first and second fibers are optical fibers and said component-detecting medium is electromagnetic radiation.

6. The method of claim 5 wherein each of said optical fibers includes a polished end making contact with said strand.

7. The method of claim 1 wherein said strand is a solid wire.

8. The method of claim 1 wherein said strand is a capillary tube.

9. The method of claim 1 wherein said removing step comprises pulling the template strand from the hardened material.

10. The method of claim 1 wherein said removing step comprises dissolution of the material of said template strand.

11. The method of claim 1 wherein, prior to the encasing step, the end of a capillary tube is slid over said template strand in close proximity thereto and extending a preselected distance therealong; and
    said capillary tube is removed after the hardening of said hardenable material.

12. The method of forming a capillary component for use in an electrophoresis instrument which comprises:
    providing a template strand having external profile dimensions and configuration complementary to the internal profile dimensions and configuration of a desired capillary component;
    disposing a tubular sleeve of light-transmitting material on a medial segment of said strand;
    contacting one side of said medial segment with a light-transmitting member and the diametrically opposite side of said segment with an optically opaque member containing an optical aperture;
    encasing said template strand within a body of hardenable material;
    hardening said hardenable material; and
    removing said template strand.

* * * * *